(12) United States Patent
Singh et al.

(10) Patent No.: US 7,414,114 B2
(45) Date of Patent: Aug. 19, 2008

(54) PROCESS FOR PREPARATION OF ANHYDROUS AZITHROMYCIN

(75) Inventors: Shiva P. Singh, Gujarat (IN); Siddiqui M. Jaweed Mukarram, Maharashtra (IN); Manish Purohit, Mahatashtra (IN); Anjum R. Khan, Aurangabad (IN)

(73) Assignee: Wockhardt Limited, Mumbai (IN)

( * ) Notice: Subject to any disclaimer, the term of this patent is extended or adjusted under 35 U.S.C. 154(b) by 0 days.

(21) Appl. No.: 10/373,349

(22) Filed: Feb. 24, 2003

(65) Prior Publication Data

US 2003/0139583 A1 Jul. 24, 2003

Related U.S. Application Data

(63) Continuation of application No. PCT/IB01/01523, filed on Aug. 23, 2001.

(60) Provisional application No. 60/227,341, filed on Aug. 23, 2000.

(51) Int. Cl.
*C07H 17/08* (2006.01)
(52) U.S. Cl. ..................................... 536/7.4
(58) Field of Classification Search ............... 536/1.5, 536/12.7, 18.5, 7.3, 120, 127, 7.4
See application file for complete search history.

(56) References Cited

U.S. PATENT DOCUMENTS

| | | | |
|---|---|---|---|
| 3,736,313 A | 5/1973 | Jones et al. ............... 260/210 E |
| 3,842,068 A | 10/1974 | Tadanier et al. ........... 260/210 E |
| 4,328,334 A | 5/1982 | Kobrehel et al. ............. 536/7.4 |
| 4,331,803 A | 5/1982 | Watanabe et al. ............. 536/7.2 |
| 4,464,527 A | 8/1984 | Bright ......................... 536/7.4 |
| 4,465,674 A | 8/1984 | Bright et al. ................. 424/180 |
| 4,474,768 A | 10/1984 | Bright ......................... 424/180 |
| 4,492,688 A | 1/1985 | Bright ......................... 424/180 |
| 4,517,357 A | 5/1985 | Kunde et al. ................ 534/605 |
| 4,517,359 A * | 5/1985 | Kobrehel et al. ............. 536/7.4 |
| 4,518,590 A | 5/1985 | Hauske et al. ................ 514/29 |
| 4,526,888 A | 7/1985 | Williams et al. .............. 514/12 |
| 4,526,889 A | 7/1985 | Bright ......................... 514/12 |
| 4,672,109 A | 6/1987 | Watanabe et al. ............. 536/7.2 |
| 4,963,531 A | 10/1990 | Remington ................... 514/29 |
| 5,110,800 A | 5/1992 | Bonjouklian et al. .......... 514/29 |
| 5,141,926 A | 8/1992 | Weber et al. .................. 514/29 |
| 5,189,159 A | 2/1993 | Wilkening ................... 540/456 |
| 5,202,434 A | 4/1993 | Wilkening ................... 540/454 |
| 5,215,980 A | 6/1993 | Jones ......................... 514/183 |
| 5,250,518 A | 10/1993 | Kobrehel et al. ............... 514/29 |
| 5,274,085 A | 12/1993 | Amano et al. ................. 536/7.4 |
| 5,332,807 A | 7/1994 | Waddell et al. ............... 536/7.4 |
| 5,350,839 A | 9/1994 | Asaka et al. .................. 536/7.4 |
| 5,441,939 A | 8/1995 | Yang .......................... 514/29 |
| 5,605,889 A | 2/1997 | Curatolo et al. ............... 514/29 |
| 5,686,587 A | 11/1997 | Yang ......................... 536/7.1 |
| 5,723,447 A | 3/1998 | Macy et al. ................... 514/29 |
| 5,808,017 A | 9/1998 | Chang ........................ 536/7.4 |
| 5,869,629 A | 2/1999 | Jasanda et al. ............... 536/7.2 |
| 5,958,888 A | 9/1999 | Macy et al. ................... 514/29 |
| 6,013,778 A | 1/2000 | Heggie et al. ................. 536/7.4 |
| 6,245,903 B1 * | 6/2001 | Karimian et al. ............. 536/7.4 |
| 6,268,489 B1 | 7/2001 | Allen et al. ................... 536/7.4 |
| 6,420,537 B1 * | 7/2002 | Bosch et al. ................. 536/7.4 |
| 6,855,813 B2 | 2/2005 | Rengaraju |
| 2005/0245469 A1 | 11/2005 | Li et al. |
| 2005/0256063 A1 | 11/2005 | Li et al. |
| 2006/0019908 A1 | 1/2006 | Mistry et al. |
| 2006/0063725 A1 | 3/2006 | Gutman |

FOREIGN PATENT DOCUMENTS

| | | |
|---|---|---|
| CA | 1191843 | 8/1985 |
| CA | 1202963 | 4/1986 |
| DE | 3 012 533 | 10/1980 |
| DE | 62-87599 | 4/1987 |
| EP | 109253 | 5/1984 |
| EP | 298650 | 1/1989 |
| EP | 0467331 A1 | 1/1992 |
| GB | 1 100 504 | 1/1968 |
| JP | 62-81399 | 4/1987 |
| WO | WO-99/58541 | 11/1999 |
| WO | WO-02/09640 | 2/2002 |

OTHER PUBLICATIONS

Djokic, Slobodan, et al., "Erythromycin Series. Part 11. Ring Expansion of Erythromycin A Oxime by the Beckmann Rearrangement", *J. Chem. Soc. Perkin Trans. I*, 1986, 1881-1891.

* cited by examiner

*Primary Examiner*—Elli Peselev
(74) *Attorney, Agent, or Firm*—Schwegman, Lundberg & Woessner, P.A.

(57) ABSTRACT

The present invention provides a stable form of azithromycin derivatives that act as antibiotics. These compounds are in anhydrous form and have increased stability over the hydrated forms.

11 Claims, 7 Drawing Sheets

PROCESS FOR PREPARATION OF ANHYDROUS AZITHROMYCIN

PRIORITY OF INVENTION

This application is a continuation Under 35 U.S.C. 111(a) of International Application No. PCT/IB01/01523 filed Aug. 23, 2001 and published as WO 02/15842 A2 on Feb. 28, 2002, which claims priority from U.S. Provisional Application No. 60/227,341, filed Aug. 23, 2000, which applications and publication are incorporated herein by reference.

BACKGROUND OF THE INVENTION

Azithromycin is a well-known semi-synthetic macrolide antibiotic. It is prepared through the ring expansion to incorporate a nitrogen atom in the macrolide ring of erythromycin A, followed by reductive methylation. This provides an antibiotic having more stability and greater effectiveness than erythromycin-A.

The ring expansion and subsequent conversion of erythromycin-A to provide azithromycin is described in U.S. Pat. No. 4,474,768, (e.g., Example 3). Generally, the synthesis requires several steps. The product obtained is one of the hydrated versions, either monohydrate or dihydrate.

Azithromycin monohydrate is hygroscopic and thus, difficult to maintain in the monohydrated form. U.S. Pat. No. 4,963,531 and EP application 298 650 teach a process for preparing azithromycin dihydrate. The process requires preparing a solution of azithromycin monohydrate in tetrahydrofuran and water. The azithromycin dihydrate is obtained by crystallization upon addition of hexane.

In U.S. Pat. No. 4,963,531 it is disclosed that on storage at low humidity the azithromycin dihydrate loses water. In addition, samples of azithromycin mono- and di-hydrate stored at higher humidity rapidly absorbed water. Thus, the water percentage (percent hydration) in the crystals can vary depending on the relative humidity during storage. This variability of the percent hydration can make it difficult to accurately determine the proper amount of active ingredient needed to prepare various dosage forms.

Thus, there is a need for forms of azithromycin that exhibit stability and less variability in the level of hydration.

SUMMARY OF THE INVENTION

The present invention provides a stable form of azithromycin and analogues thereof. These compounds are in anhydrous form that exhibits increased stability over the corresponding hydrated form. Accordingly, there is provided an anhydrous compound of Formula I:

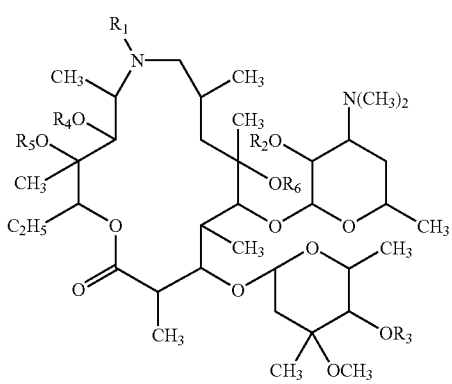

(I)

wherein $R_1$ represents hydrogen, $(C_1-C_6)$-alkyl, $(C_6-C_{10})$-aryl or $(C_7-C_{16})$-aralkyl wherein the $R_2$, $R_3$, $R_4$, $R_5$ and $R_6$ groups individually are hydrogen or $(C_1-C_6)$alkyl. The present invention also provides a process for preparing a compound of Formula I. The anhydrous compound of Formula I is prepared by a process comprising removal of an organic solvent from a solution comprising a hydrated form of the compound of Formula I in the organic solvent or a solution of the hydrated compound of Formula I in a mixture of the organic solvent and water so as to provide the anhydrous compound.

The solvents that are useful in practicing the present invention include any solvent that is capable of co-distilling with water or forming an azeotrope with water. Non-limiting examples of suitable solvents include alcohols, haloalkanes, esters, ethers or aromatic solvents. Examples of suitable solvents for practicing the invention are $C_3-C_6$ alcohols such as, for example, n-propanol, 2-propanol, n-butanol, 2-butanol, n-pentanol, 2-pentanol, 3-pentanol and the like; or halo($C_1$-$C_6$)alkanes such as, for example, methylene chloride, chloroform, carbon tetrachloride, 1,1,1-trichloroethylene, 1,1,2-trichlorethylene and the like; esters such as, for example, methyl acetate, ethyl acetate and the like; ethers such as, for example, tetrahydrofuran, tetrahydropyran and the like.

The invention also provides a pharmaceutical composition comprising an anhydrous compound of Formula I, or a pharmaceutically acceptable salt thereof, in combination with a pharmaceutically acceptable diluent or carrier.

Additionally, the invention provides a method for treating a microbial infection in a mammal, such as a human, which comprises administering, to a mammal an antimicrobially effective amount of a compound of Formula I in a suitable dosage form.

DETAILED DESCRIPTION

Figure 1:
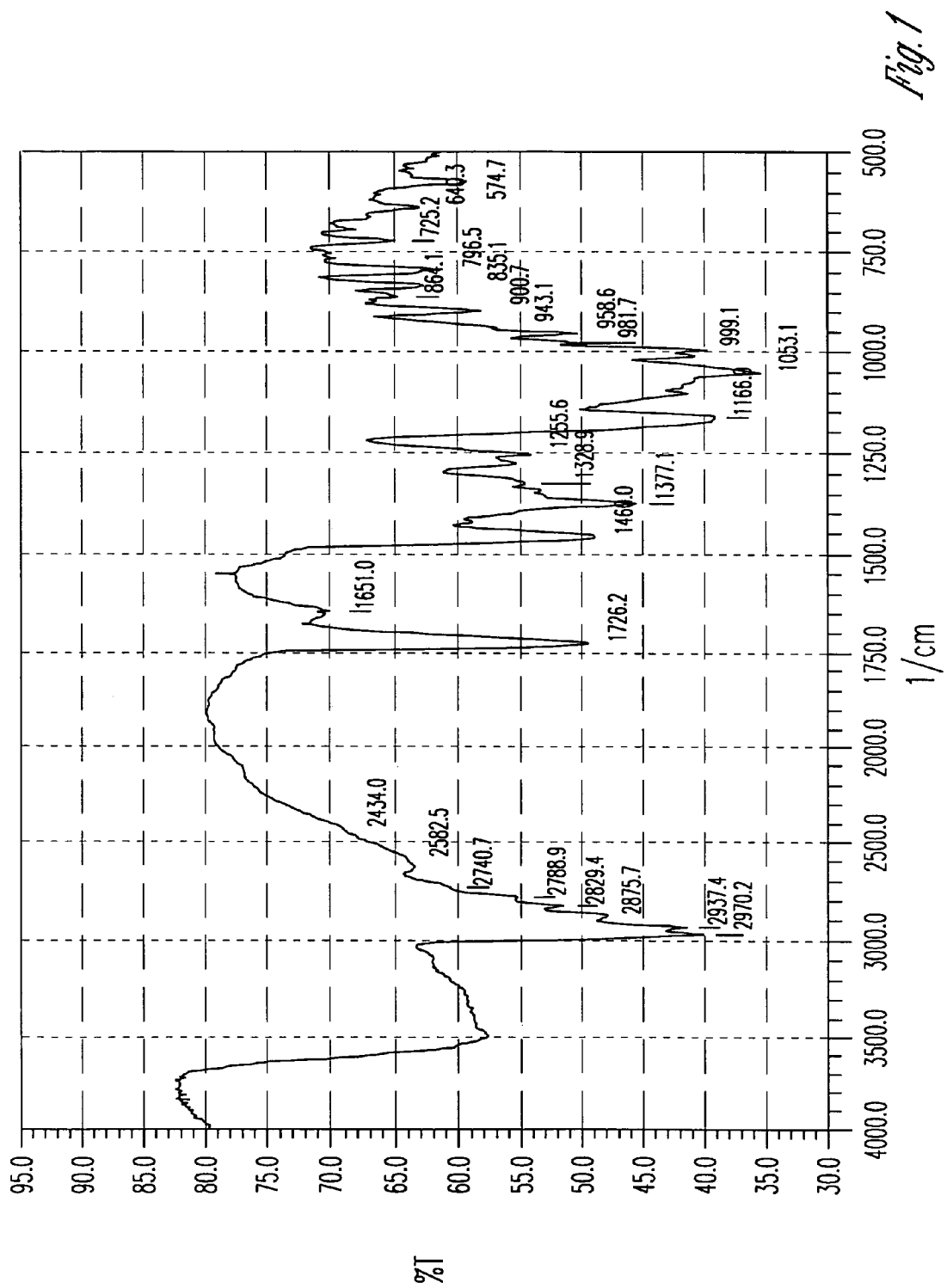
FIG. 1 illustrates the Infrared spectrum of the anhydrous azithromycin of the invention.
Figure 2:
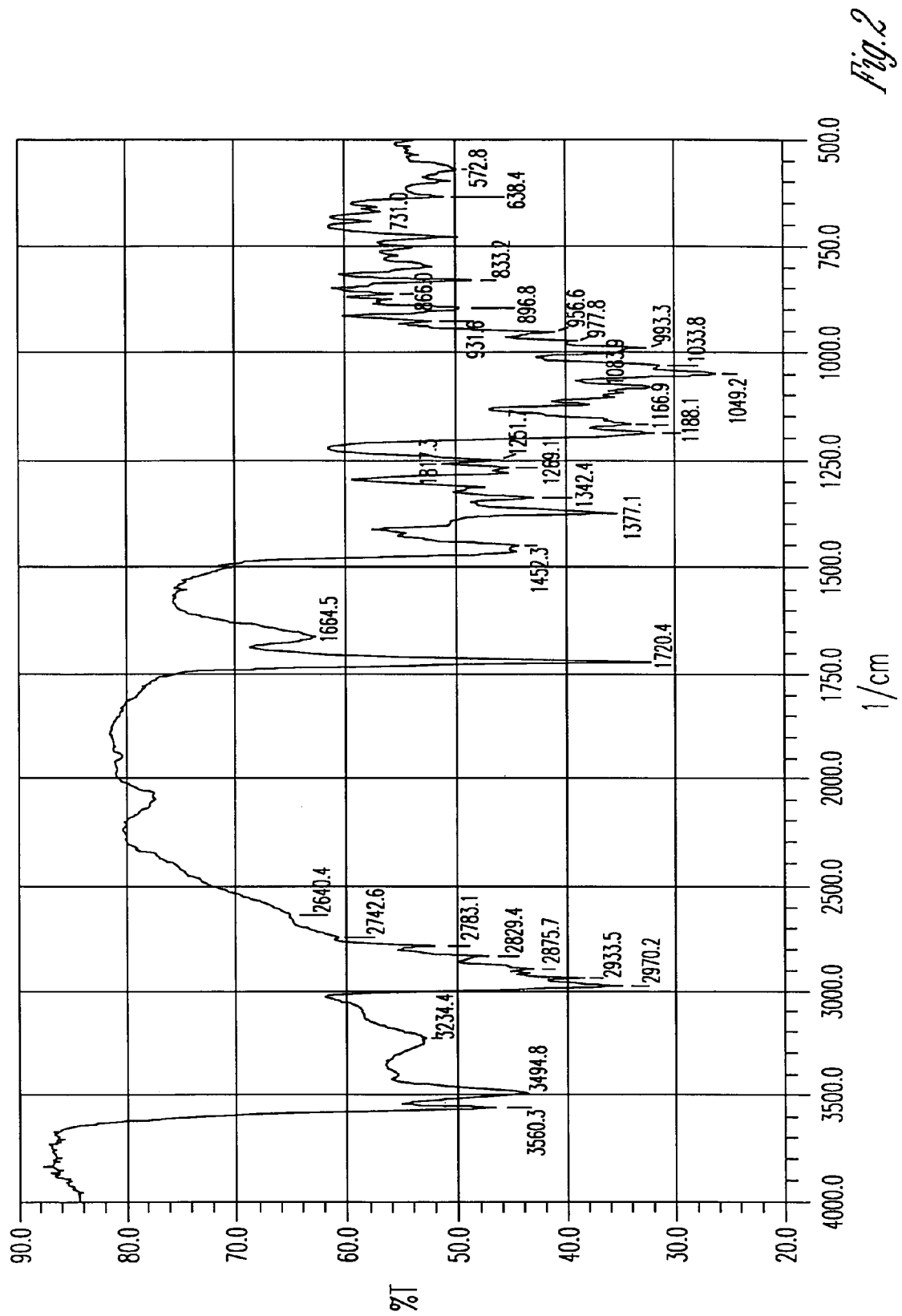
FIG. 2 illustrates the Infrared spectrum of azithromycin dihydrate.
Figure 3:
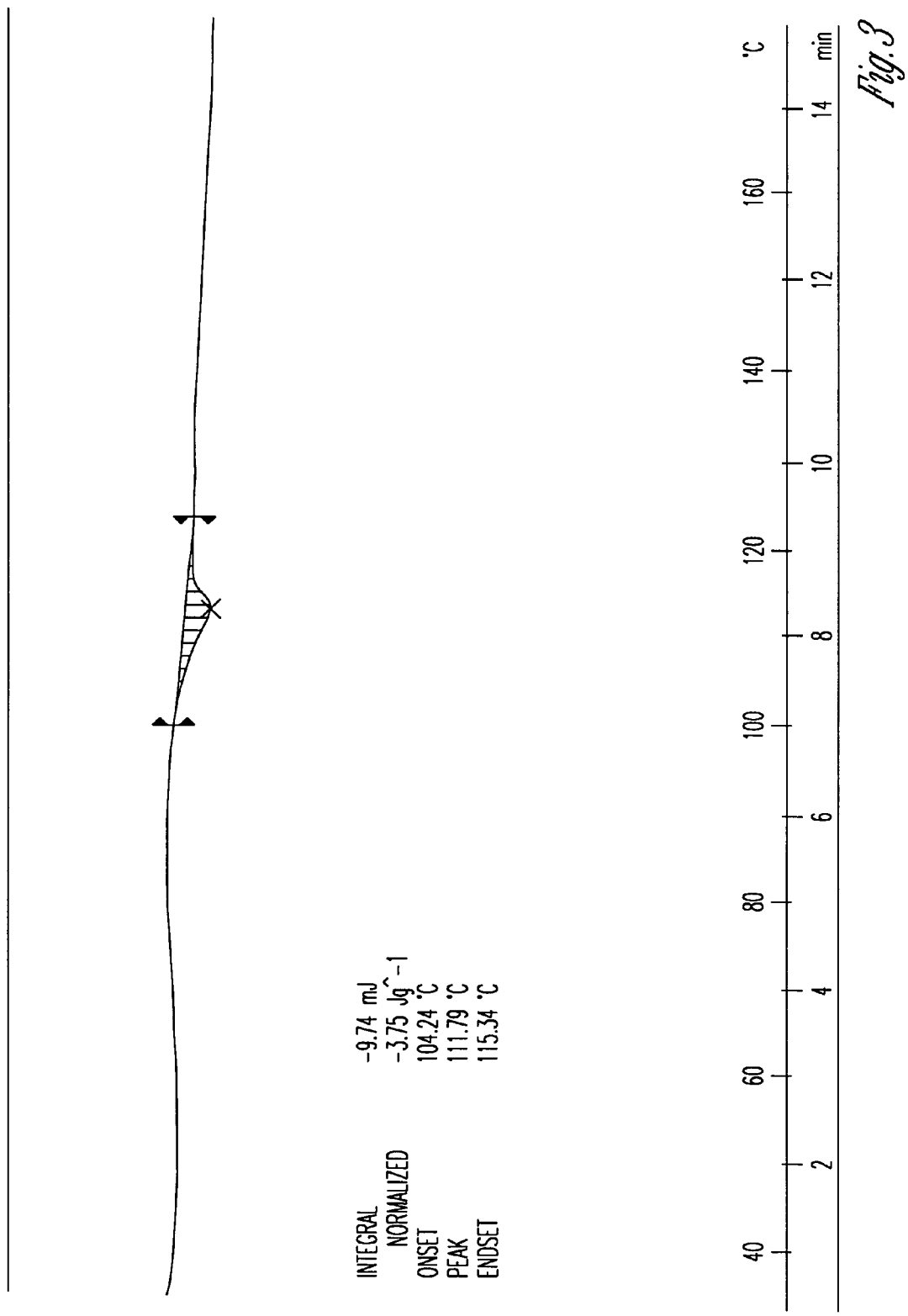
FIG. 3 illustrates the DSC spectrum of the anhydrous azithromycin of the invention.
Figure 4:
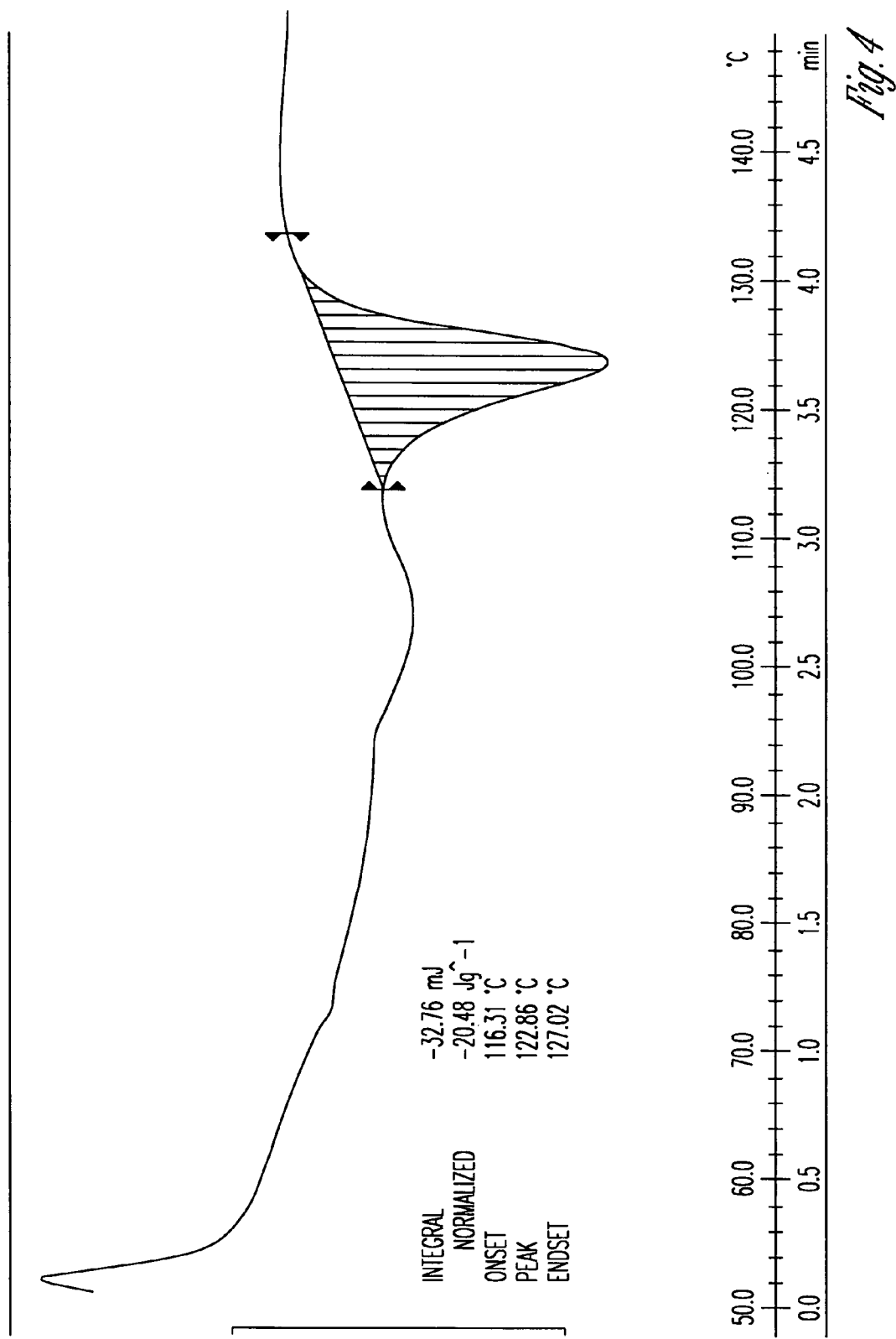
FIG. 4 illustrates the DSC spectrum of azithromycin dihydrate.
Figure 5:
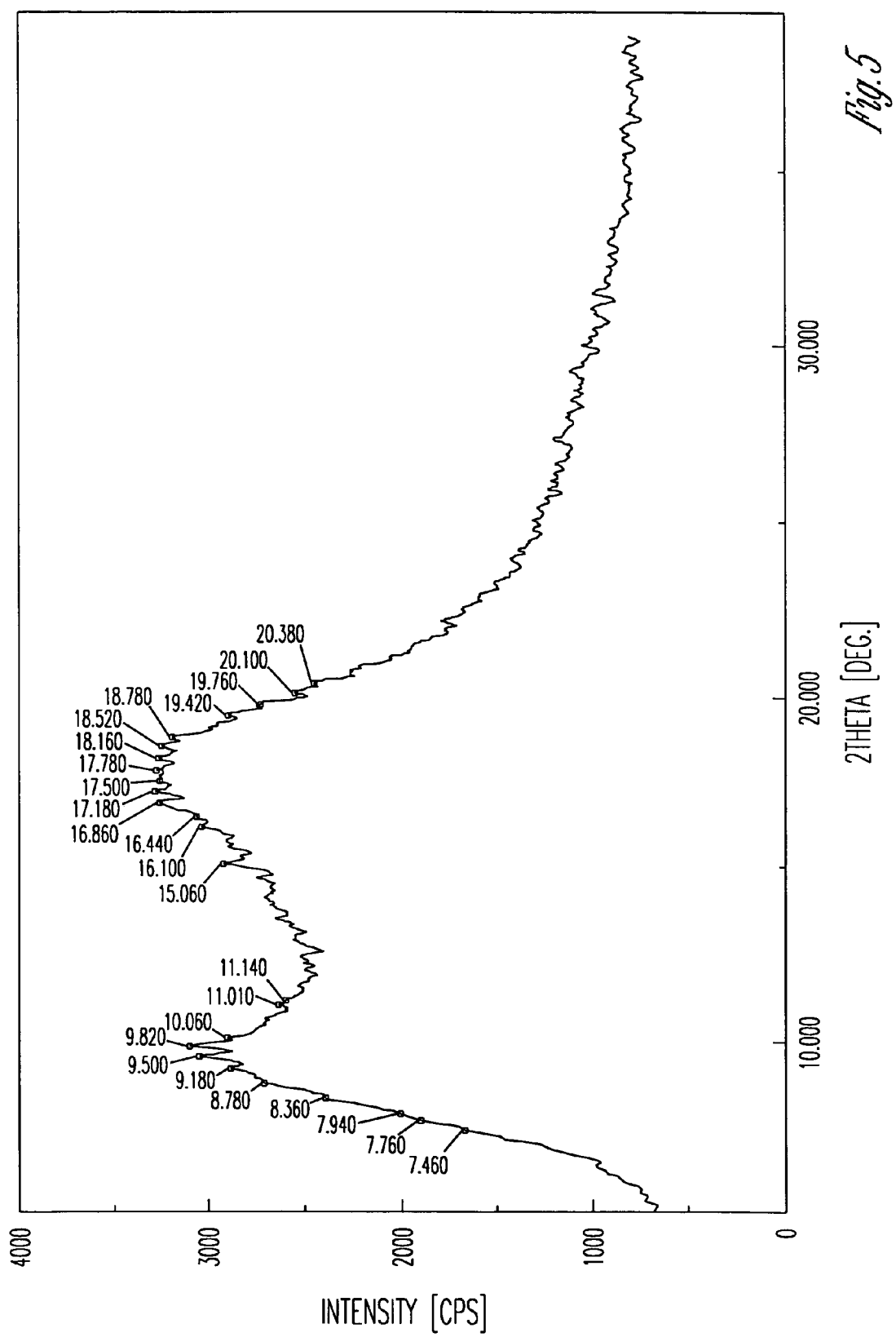
FIG. 5 illustrates the XRD spectrum of the anhydrous azithromycin of the invention.
Figure 6:
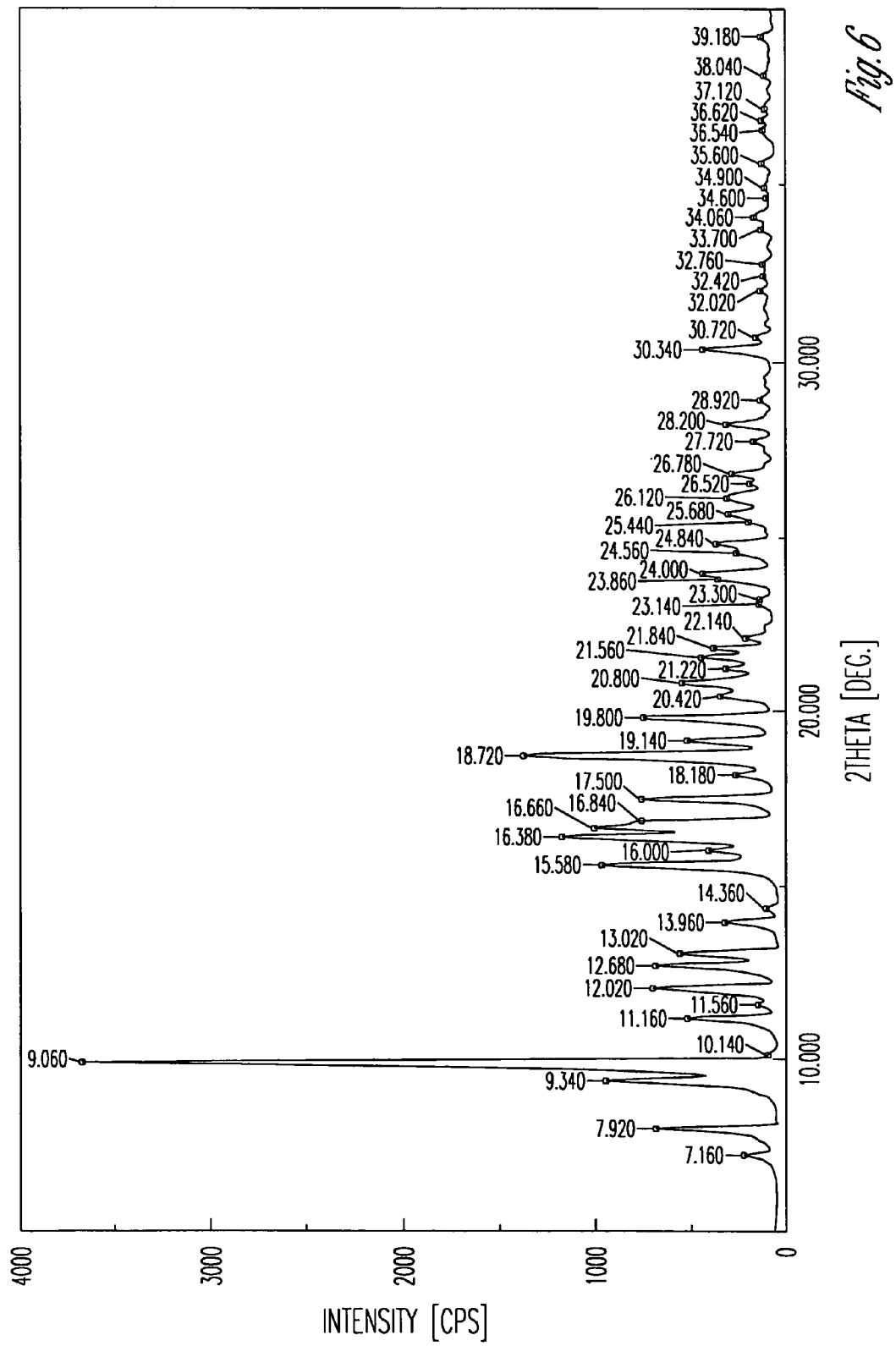
FIG. 6 illustrates the XRD spectrum of azithromycin dihydrate.

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine nicotine agonist activity using the standard tests described herein, or using other similar tests which are well known in the art.

Specific and preferred values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, n-pentyl, 2-pentyl, 3-pentyl, or hexyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $C_3-C_6$ alcohols can be 1-hydroxypropane, 2-hydroxypropane, 3-hydroxypropane, 1-hydroxybutane, 2-hydroxybutane, 1-hydroxypentane, 2-hydroxypentane, 1-hydroxyhexyl, or 6-hydroxyhexane and the like; aryl can be phenyl, indenyl, or naphthyl.

A specific value for $R_1$ is $CH_3$.

A specific value for each of $R_2$, $R_3$, $R_4$, $R_5$ and $R_6$ is hydrogen.

A preferred group of compounds are compounds of formula I; or a pharmaceutically acceptable salt thereof.

Another preferred group of compounds are compounds of formula I wherein $R_1$ is a lower alkyl group having from 1 to 4 carbon atoms and each of $R_2$, $R_3$, $R_4$, $R_5$ and $R_6$ is hydrogen.

A preferred compound of the invention is a compound of where $R_1$ is methyl and each of $R_2$, $R_3$, $R_4$, $R_5$ and $R_6$ is hydrogen or a pharmaceutically acceptable salt thereof.

The solvents that are useful in practicing the present invention include solvents that remove water from a solution either by co-distillation or azeotropic distillation. These solvents will remove small amounts of water that are difficult to remove using standard recrystallization techniques.

The preferred alcohol solvents for practicing the present invention are n-propanol, 2-propanol, n-butanol or 2-butanol. Most preferred is 2-propanol.

The preferred haloalkane solvents for practicing the present invention are methylene chloride, chloroform, and carbon tetrachloride. Most preferred is chloroform.

The preferred ester solvents for practicing the present invention are esters such as, for example, methyl acetate, ethyl acetate and the like. The preferred ester is ethyl acetate.

The preferred ether solvents for practicing the present invention are ethers such as, for example, tetrahydrofuran, tetrahydropyran and the like. The preferred ether is tetrahydrofuran.

The preferred aromatic solvents for practicing the present invention are aromatic compounds such as benzene, toluene, xylene and the like. The preferred aromatic solvent is toluene.

Figure 7:
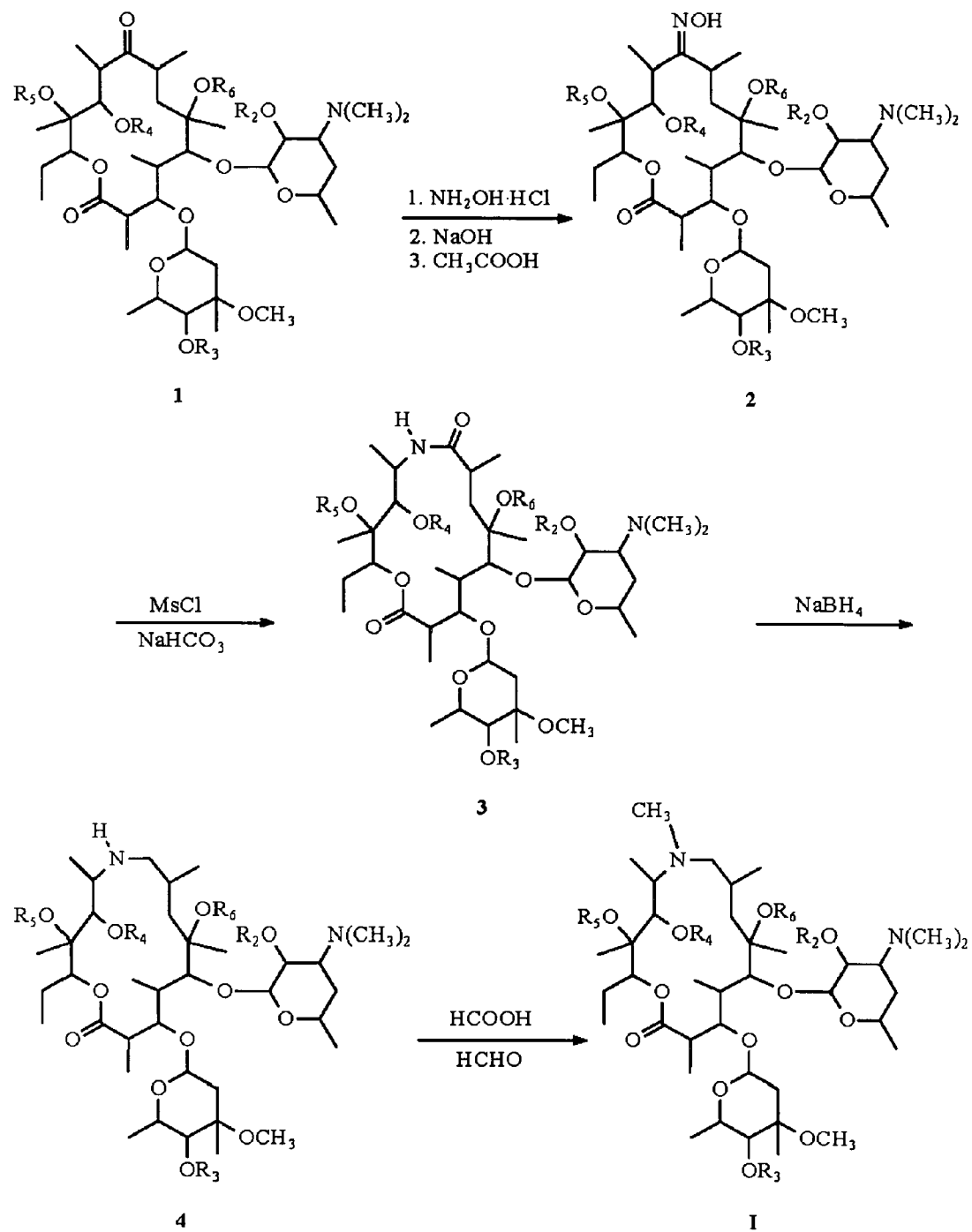
FIG. 7 illustrates the process for preparing compounds of Formula I.

The hydrated compounds useful in practicing the invention can be prepared according to the procedures disclosed in U.S. Pat. Nos. 4,328,334, 4,474,768 and 4,517,359. The process for preparing compounds of Formula I is illustrated in FIG. 7. . Compound 1, wherein $R_2-R_6$ are as defined above is converted to the corresponding oxime, 2 using an excess, e.g., about 10 equivalents, of hydroxyl amine. The oxime is rearranged via the Beckmann rearrangement with methane sulfonyl chloride at low temperature to furnish amide, 3. The amide, 3 is then reduced, with hydrogen and a catalyst or with a metal hydride, such as sodium borohydride to furnish amine, 4. The amine is then alkylated, e.g., using formaldehyde in the presence of formic acid to form the methyl analogue or by alkylation methods known in the art to form other analogues. The product is crystallized from alcohol/water to provide the hydrated compound of Formula I.

SCHEME 1

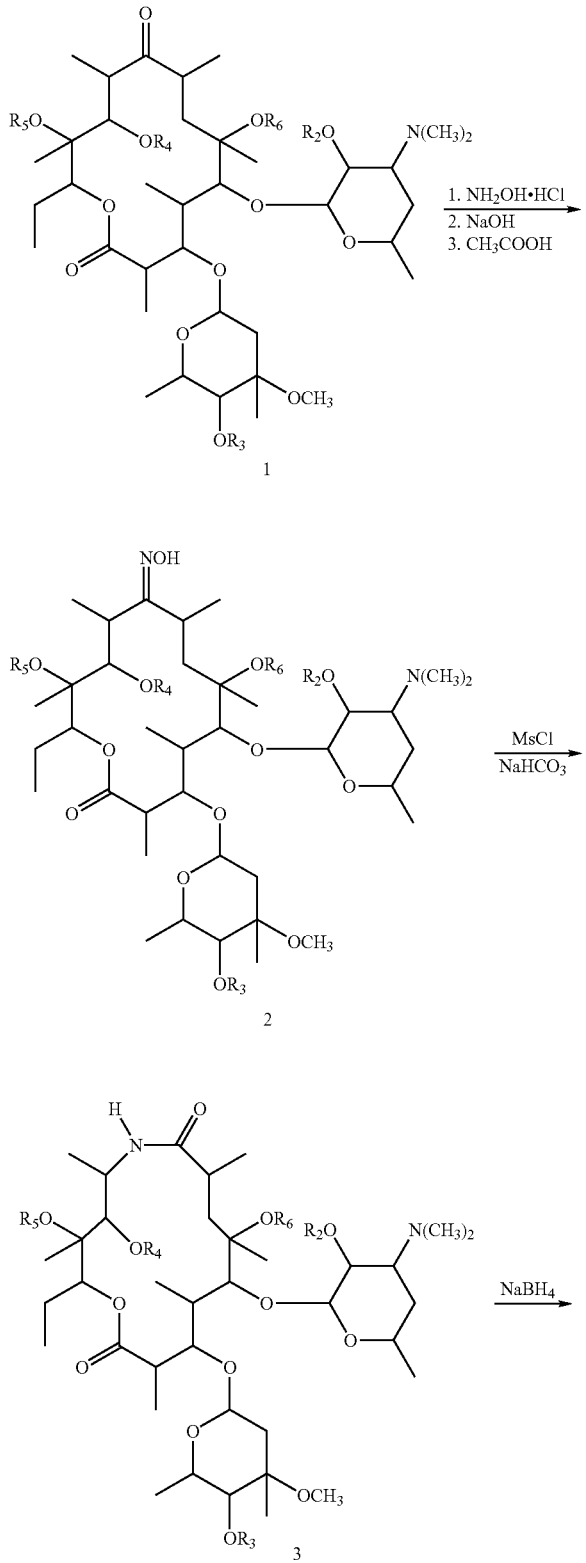

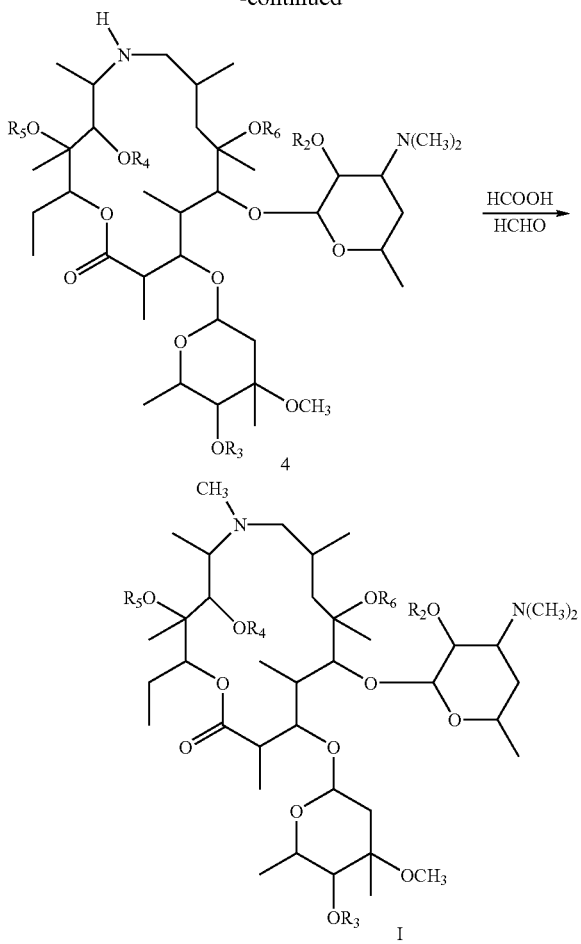

A preferred compound of the present invention, Azithromycin, is represented below:

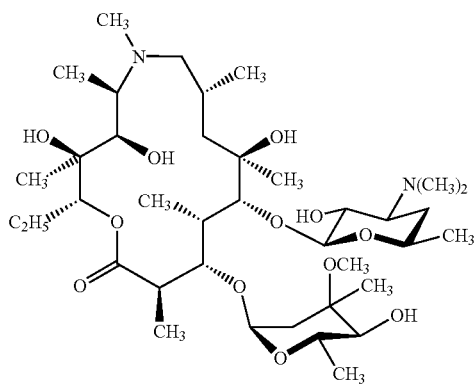

The anhydrous compounds of Formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable oral or parenteral dose will be in the range of from about 1 to about 200 mg per kilogram body weight of the recipient per day, preferably in the range of 5 to 100 mg/kg/day, most preferably in the range of 5 to 50 mg/kg/day.

The compound is conveniently administered in unit dosage form; for example, containing 25 to 3000 mg, conveniently 100 to 2000 mg, most conveniently, 250 to 600 mg of active ingredient per unit dosage form.

The invention will now be illustrated by the following non-limiting Examples.

EXAMPLE 1

Erythromtcin-A Oxime

A solution of 1.40 Kg of hydroxylamine hydrochloride in isopropyl alcohol and water was prepared. Sodium hydroxide, 0.81 Kg, was added in portions, at temperature of about 20° C. After the addition, the pH was adjusted to 7.0 with acetic acid. Erythromycin base, 1.5 Kg, was added, and the solution maintained at 45-55° C. for 28 hours.

The reaction mixture was cooled to room temperature and the reaction terminated by the addition of ammonia-water mixture. The crude product was treated with water to remove inorganic salts and furnish the title product as a white crystalline material, 1.40 Kg.

EXAMPLE 2

9a-Aza-9a-homoerythromycin-A

The title product, prepared in Example 1, 1.25 Kg, was dissolved in acetone and water and maintained at a temperature of 0-5° C. The pH of the reaction mixture was adjusted to about 2.5 to about 2.8 with hydrochloric acid. Sodium bicarbonate, 0.48 Kg, was added in portions to the cooled reaction mixture. After addition of the sodium bicarbonate, methane sulfonyl chloride, 0.5 Kg, was added. The reaction mixture was stirred for 1 hour at a temperature of 0-5° C. the pH of the reaction mixture was adjusted with aqueous sodium hydroxide and the title product was filtered off as a white crystalline material in high purity. Yield 1.00 Kg.

EXAMPLE 3

9-Deoxo-9a-aza-9a-homoerythromycin-A

The title product, prepared in Example 2, 1.00 Kg, was stirred in methanol and water. Sodium borohydride, 1 Kg, was added over four hours. The temperature was maintained below 5° C. After completion of the sodium borohydride addition, the reaction mixture was stirred for an additional six hours at <5° C. and for an additional twenty-four hours, at room temperature. The reaction was terminated by the addition of water and chloroform. The chloroform layer was separated and fresh water was added. The product was extracted with chloroform by pH adjustment using dilute hydrochloric acid and sodium hydroxide.

Initially, the mixture (water and chloroform) was stirred at pH 2.5 to 2.8 for 1 hour. The pH of the water layer was adjusted to 9.5 to 9.8, and the mixture was stirred for one-half hour. This sequence was repeated with additional chloroform three times. The water layer was separated and an additional portion of chloroform was added and the extraction repeated one additional time. After the extraction, the chloroform extracts were combined, dried over potassium carbonate, filtered and used in the next step without additional treatment.

EXAMPLE 4

9-Deoxo-9a-methyl-9a-aza-9a-homoerythromycin-A

The title product, prepared in Example 3, was treated with formaldehyde, 0.17 L, and formic acid, 0.105 L, the reaction mixture was stirred for four hours, under nitrogen and heated at reflux for twelve hours. The reaction was cooled, treated with water and the pH was adjusted to 4.0 to 4.5. Chloroform was added and the mixture stirred and the chloroform layer separated. The aqueous layer was adjusted to pH 6.0 to 6.5 and extracted twice with chloroform. Additional chloroform was added to the aqueous layer and the pH was adjusted with stirring to about pH 2.0 to 3.0 with dilute hydrochloric acid. The mixture was stirred vigorously and the chloroform layer was separated. The pH was adjusted to about pH 6.0-6.5 with dilute sodium hydroxide and extracted twice with chloroform.

This sequence above was repeated five times on the aqueous layer. The chloroform layers were combined, dried over $K_2CO_3$ and concentrated under vacuum. The solid residue was dissolved in isopropyl alcohol and the title product crystallized by adding water. The yield of azithromycin was 0.55 Kg.

EXAMPLE 5

Azithromycin Dihydrate

The title product, 0.5 Kg, prepared in Example 4, was dissolved in water, making the solution acidic (pH of 2.5 to 5.0) with dilute hydrochloric acid. After 20 minutes stirring the pH was raised with dilute sodium hydroxide and the solution was stirred for twelve hours. The product was crystallized as a white crystalline material in high purity. Yield: 0.48 Kg.

EXAMPLE 6

Anhydrous Azithromycin

The azithromycin dihydrate, prepared in Example 5, or the azithromycin monohydrate, prepared in Example 4, about 500 g, was dissolved in isopropanol, 3 L. The solution was heated and the alcohol was distilled to remove the water. After the solvent was removed the residue was dried under vacuum to provide the anhydrous azithromycin. Yield 470 g; Purity≧96%.

EXAMPLE 7

Anhydrous Azithromycin

The azithromycin dihydrate, prepared in Example 5, or the azithromycin monohydrate, prepared in Example 4, ~100 g, was dissolved in chloroform and water, 1.7 L (0.7:1). The solution was heated and the solvent was distilled off. After the solvent was removed the residue was dried under vacuum to provide the anhydrous azithromycin. Yield 94 g; Purity≧96%.

All publications, patents, and patent documents cited in the specification are incorporated by reference herein, as though individually incorporated by reference. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

The invention claimed is:

1. A process for preparing an anhydrous compound having formula I:

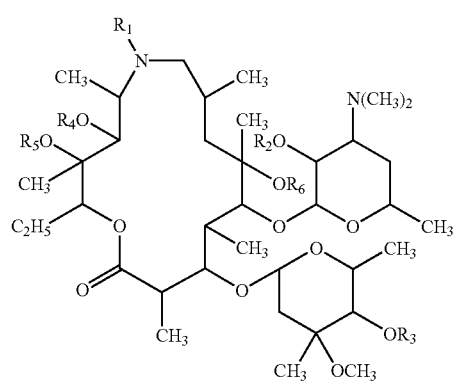

(I)

wherein $R_1$ represents hydrogen, $(C_1\text{-}C_6)$-alkyl, $(C_6\text{-}C_{10})$-aryl or $(C_7\text{-}C_{16})$-aralkyl; and each $R_2$, $R_3$, $R_4$, $R_5$ and $R_6$ individually represents hydrogen or $(C_1\text{-}C_4)$alkyl; consisting essentially of removing, by distillation, a halo$(C_1\text{-}C_6)$alkane solvent from a solution prepared by dissolving a hydrated compound of Formula I and water in the halo$(C_1\text{-}C_6)$alkane solvent so as to provide the anhydrous compound through removal of the water from the solution by co-distillation or azeotropic distillation of the water with the solvent.

2. A process according to claim 1, wherein the solvent is a halo $(C_1\text{-}C_5)$ alkane.

3. A process according to claim 2, wherein the haloalkane solvent is selected from the group consisting of methylene chloride, chloroform, carbon tetrachloride, 1,1,1-trichloroethylene, and 1,1,2-trichlorethylene.

4. A process according to claim 3, wherein the solvent is selected from the group consisting of methylene chloride, chloroform, and carbon tetrachloride.

5. A process according to claim 4, wherein the solvent is chloroform.

6. A process according to claim 1, wherein each $R_1$, $R_2$, $R_3$, $R_4$, $R_5$ and $R_6$ is hydrogen.

7. A process according to claim 1, wherein $R_1$ is $(C_1\text{-}C_6)$-alkyl, $(C_1\text{-}C_{10})$-aryl or $(C_1\text{-}C_{16})$-aralkyl and each $R_2$, $R_3$, $R_4$, $R_5$ and $R_6$ is hydrogen.

8. A process according to claim 7, wherein $R_1$ is $(C_1\text{-}C_6)$-alkyl.

9. A process according to claim 8, wherein $R_1$ is methyl or ethyl.

10. A process according to claim 9, wherein $R_1$ is methyl.

11. A process according to claim 1, wherein the hydrated compound of Formula I is azithromycin monohydrate, azithromycin dihydrate or a mixture thereof.

* * * * *

UNITED STATES PATENT AND TRADEMARK OFFICE
CERTIFICATE OF CORRECTION

PATENT NO. : 7,414,114 B2
APPLICATION NO. : 10/373349
DATED : August 19, 2008
INVENTOR(S) : Singh et al.

Page 1 of 1

It is certified that error appears in the above-identified patent and that said Letters Patent is hereby corrected as shown below:

On the Title Page, Item (75), in "Inventors", line 3, delete "Mahatashtra" and insert -- Maharashtra --, therefor.

In column 7, line 40, delete "Erythromtcin-A" and insert -- Erythromycin-A --, therefor.

In column 10, lines 17-18, in Claim 3, delete "tetrachioride, 1,1,1 -trichioroethylene," and insert -- tetrachloride, 1,1,1-trichloroethylene, --, therefor.

In column 10, line 29, in Claim 7, delete "$(C_1-C_{10})$-aryl or $(C_1-C_{16})$" and insert -- $(C_6-C_{10})$-aryl or $(C_7-C_{16})$ --, therefor.

Signed and Sealed this

Eighteenth Day of November, 2008

JON W. DUDAS
*Director of the United States Patent and Trademark Office*